US005474524A

United States Patent [19]
Carey

[11] Patent Number: 5,474,524
[45] Date of Patent: Dec. 12, 1995

[54] JOINT SUPPORT

[76] Inventor: Michael J. Carey, 6817 Elaine Way, San Diego, Calif. 92120

[21] Appl. No.: 957,696

[22] Filed: Oct. 7, 1992

[51] Int. Cl.$^6$ .............................. A61F 5/00; A61F 13/00
[52] U.S. Cl. .................. 602/26; 602/23; 602/14; 602/62; 602/63
[58] Field of Search .................. 602/1, 3, 60, 61, 602/62, 63, 64, 65, 26, 14, 20, 23; 128/882, 869

[56] References Cited

U.S. PATENT DOCUMENTS

| | | | |
|---|---|---|---|
| 366,590 | 7/1887 | Lubin | 602/60 |
| 663,749 | 12/1900 | Gorse | 602/60 |
| 1,727,897 | 9/1929 | Myers et al. | 602/60 |
| 4,084,586 | 4/1978 | Hettick | 602/60 |
| 4,474,573 | 10/1984 | Detty | 602/26 |
| 4,492,227 | 1/1985 | Senn et al. | 602/63 |
| 4,632,106 | 12/1986 | Gamm | 602/63 |
| 5,092,318 | 3/1992 | More et al. | 602/63 X |
| 5,139,477 | 8/1992 | Peters | 602/26 |
| 5,185,000 | 2/1993 | Brandt et al. | 602/63 |

*Primary Examiner*—Robert A. Hafer
*Assistant Examiner*—Brian E. Hanlon
*Attorney, Agent, or Firm*—Trask, Britt & Rossa

[57] ABSTRACT

A tubular support for positioning about a body joint is made of closed-cell neoprene and has an opening with an insert therein of a thinner elastic material to provide breathability and avoid bunching when flexing the joint. The thinner material of the insert is preferably attached to a frame that is then secured in the opening prior to forming the panel into the tubular shape.

13 Claims, 1 Drawing Sheet

5,474,524

JOINT SUPPORT

BACKGROUND OF THE INVENTION

1. Field of the Invention

The present invention pertains to a support for articulated joints of the body, such as knees, elbows, and the like, and, more particularly, to a support formed of elastically deformable material having an insert of thinner elastically deformable material for positioning proximate the joint.

2. State of the Art

Braces or supports for positioning about an articulated body joint such as the knee, ankle, wrist or elbow are well known. Such supports may be used to provide support or to provide other therapeutic benefits.

One class of support is formed of an elastic material such as a closed-cell neoprene offered by Rubatex Corporation of Bedford, Va. One example of such a support is offered by PRO Orthopedic Services, Inc., P.O. Box 31401, Tucson, Ariz. 85726. Other similar elastic-type supports without mechanical structures are typically available.

Known supports can cause discomfort to the user. When the user rotates a limb or body member in relation to an adjoining member, as when the lower leg is rotated rearward and upward about the knee, the knee flexes and the popliteal area behind the knee compresses. Due to the thickness of the support, the material behind the knee in the popliteal area tends to gather or bunch. In turn, the user may experience irritation and discomfort when the knee is repeatedly rotated rearward or flexed.

One proposed method for correcting this condition is disclosed in U.S. Pat. No. 4,474,573 (Lerman) for a knee sleeve. As taught therein, the area of the sleeve that is adjacent the popliteal area behind the knee is constructed of an elastic material with a diamond-shaped patch of the same material. The patch has its two side points on the forward portion of the knee. The seams where the material is attached to the sleeve thereby circumvent the popliteal area. However, the material in the popliteal area is still of the same thickness as the sleeve so that bunching and irritation is expected to still be a problem.

Thus, a need remains for a support that provides adequate support for a joint and comfort for the user in use.

SUMMARY OF THE INVENTION

The present invention is directed to a support for a joint that comprises a sleeve of elastically deformable material sized and shaped to fit snugly over the joint. The sleeve has a first opening formed in it for positioning proximate the body joint. An insert is formed of an elastically deformable material which is thinner than the thickness of the material of the sleeve. Ideally, the insert is secured in the opening of the sleeve in tension to urge relative movement of a first body member relative to a second body member, each being rotatable relative to each other in a preselected direction about the body joint. The sleeve is preferably formed of a closed cell neoprene material and the insert is preferably formed of lycra.

In an alternative arrangement, the support includes a second insert formed of elastically deformable material that is substantially of the same thickness as the material of the sleeve. The second insert has an inside edge that defines a second opening and an outside edge that defines the circumference of the second insert and corresponds to the edge of the first opening. Ideally, the first insert is secured to the inside of the second insert in tension.

While the second insert preferably has a diamond shape, other shapes may also be used.

In accordance with yet another aspect of the present invention, the support is formed in a predetermined shape to more precisely conform to the shape of the joint. The support is slightly bent to match the natural bend of the applicable joint by sewing one or more darts in the tubular-shaped panel of stretchable material. These darts are ideally formed transverse to the longitudinal axis of the tubular support and intersect the sides of the frame.

BRIEF DESCRIPTION OF THE DRAWINGS

In the drawings, which presently illustrate what is believed to be the preferred mode for carrying out the invention.

DETAILED DESCRIPTION OF ILLUSTRATED EMBODIMENT

An articulated joint such as a knee joint, elbow joint, wrist or ankle interconnects a first body member and a second body member for rotation relative to each other about the joint between a first position in which the first body member and said second body member are in general alignment and a second position in which said first body member and said second body member are rotated about the body joint to a preselected angle. The body members are in general alignment as, for example, when the body joint is a knee and the person is standing upright with the legs straight.

Figure 1:
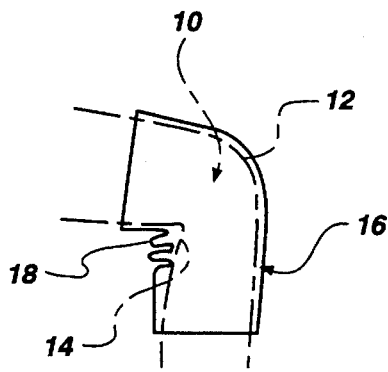
FIG. 1 is a side view depiction of a prior art support placed on a flexed knee joint.

The joint may be said to have an exterior side that stretches and an interior side that compresses when the first body member rotates relative to the second (i.e., flexes). For example, referring initially to FIG. 1, a knee joint 10 is illustrated in phantom and has an exterior side referred to as the patella 12 and an interior side commonly referred to as the popliteal 14. A prior art knee sleeve 16 of typical construction is also depicted. As can be seen in FIG. 1, the material 18 bunches up in the popliteal area 14 when the knee joint 10 is fully flexed. The bunched up material 18 is shown out of proportion for clarity. The bunched material can cause irritation and discomfort to the user in the popliteal area 14. At the same time, the material in the patella region 12 may distort excessively and move relative to the skin to also cause some irritation or discomfort.

Figure 2:
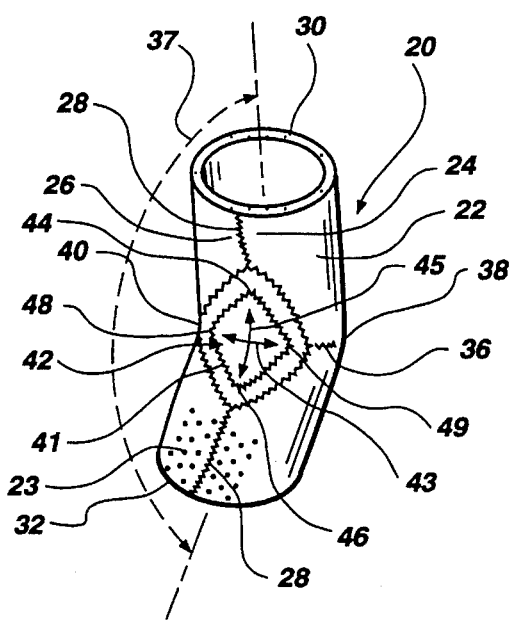
FIG. 2 is a perspective rear view of a knee support formed in accordance with the present invention.

Referring next to FIG. 2, a knee support 20 of the present invention has a sleeve 22 formed of an elastically deformable material, preferably a closed-cell neoprene, which can be obtained from Rubatex Corporation, P.O. Box 340, Bedford, Va. 24523. It has been found that closed-cell neoprene having a thickness in the range of about 2 cm to about 4 cm with a preferred thickness of about 3 cm provides adequate support for the knee without being cumbersome or uncomfortable.

A most preferred material is a closed-cell neoprene with a pattern of very small holes 23 or perforations formed therein. The individual holes may range in cross section from as small as 0.01 square centimeters to larger than 0.1 square centimeters. The small holes may be considerably larger in some applications; but the smaller holes have been found preferable for the illustrated embodiment. The holes are believed to facilitate air communications with the skin and in turn allow moisture to evaporate to reduce moisture buildup without adversely affecting the strength of the material and the support provided when in place. At the same time, the material 22 retains sufficient heat to provide the perceived therapeutic benefit which may be attributed to retained body heat. An open-cell material may also be used in some applications.

The sleeve 22 is formed into a tubular shape by stitching the opposing edges 24 and 26 (FIG. 4) together to form a butt seam 28. In the illustrated embodiment of FIGS. 2 and 4, no hem or other edge facing is placed or formed on the top and bottom edges 30 and 32. The sleeve 22 is made in different sizes for different people and is sized and shaped so that it will snugly fit over and support the joint and upper and lower areas proximal thereto.

Figure 4:
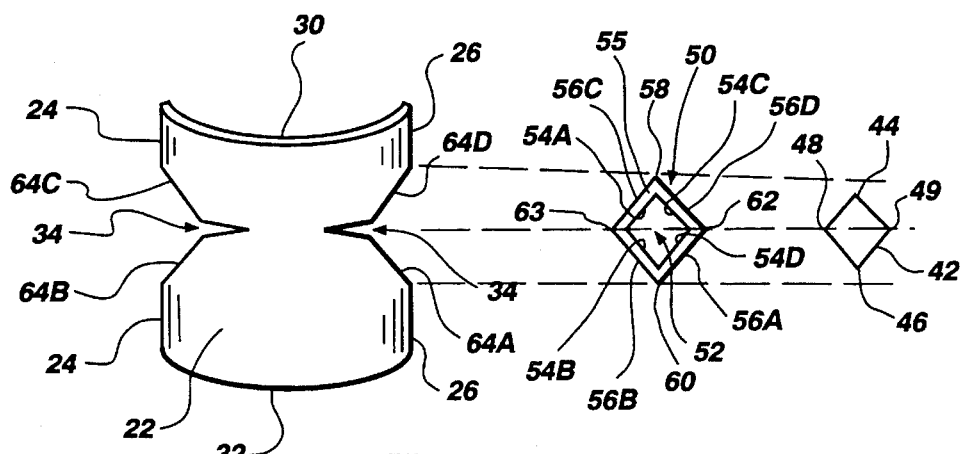
FIG. 4 is an exploded view showing the components of the knee support formed in accordance with the method of construction of the present invention.

As shown more clearly in FIG. 4, slits 34 are formed in the edges 24 and 26 of the panel 22. The slits 34 are sewn together to form darts 36 as shown in FIG. 2. The darts 36 act to give the support 20 an angle 37 so that the support 20 is tensioned for a knee joint in the popliteal area 14 and compressed in the patella area 12 when the user is standing with the leg straight. Thus, when the user flexes the knee, there is less tendency for material to bunch up in the popliteal area 14 as in the prior art devices. Indeed, for walking and other normal flex situations, the support 20 is more comfortable in use. Of course at a convenient position with the angle 37 of about 150°, the support 20 including the insert is at rest with what may be said to be zero tension as to the body joint.

For other joints, the angle 37 may be selected consistent with the joint. For example, the angle 37 for the knee may be from about 150° to about 170°. The angle 37 for the elbow may be from about 120° to about 160°.

Positioned proximate the center of the support 20 at the inside portion 40 is an insert 42. Thus, when the support 20 is placed on the knee, the insert 42 is formed to be positioned over the popliteal area 14. The insert 42 is constructed of material that is substantially thinner than the panel 22 and is itself elastically deformable and breathable. In the illustrated embodiment, a thin lycra material is preferred.

The insert 42 is positioned within a corresponding first opening formed in the sleeve 22. That is, a first opening 41 is formed on the inside portion of the sleeve 22 to extend in width 43 at least the width of the joint and in height a preselected distance 45 sufficient to minimize bunching up of the material of the sleeve 22. Although the height 45 may vary for the joint involved as well as for aesthetics, a height 45 of at least about one half the width 43 is believed to be sufficient with the preferred height 45 approximately the same as the width 43.

As shown, a diamond shape insert 42 is preferred. However, it is to be understood that other geometric shapes may be used, such as an oval or a circle. As shown in FIG. 2, the insert 42 is positioned so that the top corner 44 and bottom corner 46 are in alignment with the longitudinal butt seam 28. The side corners 48 and 49 are preferably in alignment with the darts 36.

To minimize the bunching of material when the first limb is rotated toward the second limb to a maximum flex with the support 20 positioned about a joint, the insert 42 may be sized to be less than the dimensions of the opening 41. Thus, the insert is in tension when the support 20 is positioned about the joint with the first body member and second body member rotated about the joint to a minimum flex or to be in general axial alignment as when a user with a knee support in place is standing upright with the user's legs straight. When the limbs are at a maximum flex, the angle 37 is at its smallest; and when at the minimum flex, the angle 37 is at its largest flex or close to 180°.

Because it is difficult to form a butt seam between two materials having differing thicknesses when the materials are in tension, and, more specifically, when forming the material into a sleeve 22 such as with the support 20 of the present invention, a second insert or frame 50 is provided. The frame 50 is formed of elastically deformable material substantially the same, and preferably the same, as the elastically deformable material of the sleeve 22. In the preferred embodiment, both the sleeve 22 and the frame 50 are formed from the same neoprene material.

As best seen in FIG. 4, the frame 50 has a second opening 52 that is defined by interior edges 54A, 54B, 54C and 54D. The circumscribing exterior edges 56A, 56B, 56C and 56D of the frame 50 are cut into a diamond shape such that the frame 50 has top and bottom corners 58 and 60 and side corners 62 and 63. Similarly, the interior edges 54A-D of the sleeve 22 that form the second opening 52 are also cut in a diamond shape that substantially conforms to the diamond shape of the insert 42. The panel 22 has angled edges 64A, 64B, 64C and 64D cut into both side edges 24 and 26 that match the size and shape of the exterior edges 56A-D of the frame 50. Thus, when the sleeve 22 is sewn together, the angled edges 64A-D form a diamond-shaped opening to receive the frame 50. Similarly, the insert 42 is inserted into the opening 52 of the frame 50.

In accordance with the method of construction of the present invention, the sleeve 22 is first cut out of the elastically deformable material in the pattern shown in FIG. 4. The slits 34 that eventually are used to form the darts 36 are optional. That is, darts are used if it is desirable to pre-bend the support 20.

In similar fashion, the frame 50 is also cut, preferably from the same material as the panel 22. The insert 42 is cut from differing material which was described above.

The insert 42 is then sewn to the frame 50 along the interior edges 54A-D to fill the second opening 52. To provide maximum comfort, the insert 42 is sewn so as to be flush with the inside surface 55 of the frame 50. Furthermore, the insert 42 is placed under tension prior to sewing to the frame 50.

If darts 36 are to be used, the slits 34 are sewn together prior to stitching of the frame 50 to the panel 22. Two of the exterior edges of the frame 50 are sewn to the matching angled edges 64 on the panel 22. At this point, all of the stitching can be done when the material is flat, thus facilitating attachment of the insert 42 to the thicker frame 50.

After the frame 50 has two of its exterior edges 56A and 56B sewn to the angled edges 64A and 64B, the matching edges 24 and 26 of the panel are brought together and sewn. Thereafter, the remaining exterior edges 56B and 56C of the frame 50 are sewn to the angled edges 64C and 64D. This method of construction overcomes the problem of sewing dissimilar thickness materials together in tension while forming a sleeve or tubular shape. In addition, it provides seams that have less bulk and, consequently, are more comfortable to the user.

As apparent, the support 20 illustrated is a knee support.

Those skilled in the art may readily vary the dimensions as necessary to form an elbow support, an ankle support, a wrist support or the like.

Figure 3:
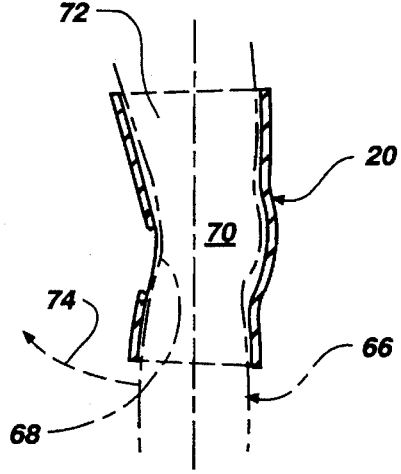
FIG. 3 is a side view in cross-section of the knee support of FIG. 1 placed over a knee joint.

A completed knee support 20 is shown in FIG. 3. In use, the support 20 is pulled up over the lower leg 66 (first body limb) and positioned about the joint 70 with the insert 42 placed over the popliteal area 68. As the knee joint 70 is flexed, the lower leg 66 (first body limb) rotates relative to the upper leg 72 (second body limb). In turn, the insert 42 is in tension with the upper leg 72 and lower leg 66 in general axial alignment as shown. As the lower leg 66 rotates toward 74 the upper leg 72, the insert 42 relaxes and conforms to the shape of the popliteal area 68. Irritation and discomfort due to bunching of excessively thick material is thereby minimized. As noted, when the lower leg 66 is straightened toward axial alignment, the insert 42 stretches. In turn, the insert 42 and support 20 provide support to the knee joint 70. Because it is made of a thin, breathable material, the insert 42 also enhances breathability in the popliteal area 68.

While a preferred embodiment of the invention has been illustrated and described, it is to be understood that various changes may be made therein without departing from the spirit and scope of the invention. For instance, while butt seams have been described as the preferred embodiment, it is possible that other seams may be used. In addition, attachment of the materials can be undertaken by stapling, adhesives, or the like. Also, nonbreathable material may also be used to achieve substantially the same results. Finally, while a single panel 22 has been described as being used to form the invention, which is less labor intensive than using multiple panels, it is possible to use multiple panels without departing from the spirit and scope of the invention. Consequently, the invention is to be limited only by the scope of the claims that follow.

We claim:

1. A method of constructing a support for positioning about a body joint in which a first body member extends away therefrom and a second body member extends away therefrom and rotates about said body joint relative to said first body member between a first position in which said first body member and said second body member are in general alignment and a second position in which said first body member and said second body member are rotated about said body joint to a preselected angle, said method comprising the steps of:

providing a first elastically deformable material having a thickness;

forming a sleeve with open opposite ends from said first elastically deformable material, said sleeve having a first opening formed for positioning proximate said body, joint;

providing a second elastically deformable material having a thickness substantially the same as the thickness of said first elastically deformable material;

forming a first insert from said second elastically deformable material sized for positioning in said first opening;

forming a second opening in said first insert;

providing a third elastically deformable material having a thickness substantially less than the thickness of said first elastically deformable material;

forming a second insert from said second elastically deformable material sized for positioning in said second opening;

securing said second insert in said second opening to be in tension when said first insert is positioned in said first opening and said support is positioned proximate said body joint with said first body member and said second body member in said first position; and securing said first insert in said first opening.

2. A method of constructing a support for positioning about a body joint in which a first body member extends away therefrom and a second body member extends away therefrom and rotates about said body joint relative to said first body member between a first position in which said first body member and said second body member are in general alignment and a second position in which said first body member and said second body member are rotated about said body joint to a preselected angle, said method comprising the steps of:

providing a first elastically deformable material having a thickness;

forming one or more darts in said first elastically deformable material such that the support will be bent at a preselected angle;

forming a sleeve with open opposite ends from said first elastically deformable material, said sleeve having a first opening formed for positioning proximate said body joint;

providing a second elastically deformable material having a thickness substantially the same as the thickness of said first elastically deformable material;

forming a first insert from said second elastically deformable material sized for positioning in said first opening;

securing said first insert in said first opening to be in tension when said first body member and said second body member are in said first position;

forming a second opening in said first insert;

providing a third elastically deformable material having a thickness substantially less than the thickness of said first elastically deformable material;

forming a second insert from said third elastically deformable material sized for positioning in said second opening; and securing said second insert in said second opening to be in tension when said first insert is positioned in said first opening and said support is positioned proximate said body joint with said first body member and said second body member in said first position.

3. The method of claim 2 wherein the first elastically deformable material is formed from closed cell neoprene.

4. A method of constructing a knee support comprising the steps of:

providing a first elastically deformable material having a thickness;

forming a panel from said first deformable material;

providing a second elastically deformable material having a thickness substantially the same as the thickness of the first elastically deformable material;

forming a frame of the second elastically deformable material having an opening therein sized and shaped to receive an insert;

providing a third elastically deformable material having a thickness that is thinner than said first elastically deformable material;

forming said insert of said third elastically deformable material;

attaching the insert to the frame to cover the opening and to be in tension in the frame;

attaching a portion of the frame to the panel; and forming the panel into a sleeve with the frame secured therein for positioning proximate a flexible limb joint of a user.

5. A method of constructing a knee support comprising the steps of:

providing a first elastically deformable material having a thickness;

forming a panel from said first deformable material;

forming one or more darts in said panel such that the knee support will be bent at a preselected angle;

providing a second elastically deformable material having a thickness substantially the same as the thickness of the first elastically deformable material;

forming a frame of the second elastically deformable material having an opening therein sized and shaped to receive an insert;

providing a third elastically deformable material having a thickness that is thinner than said first elastically deformable material;

forming said insert of said third elastically deformable material;

attaching the insert to the frame to cover the opening and to be in tension in the frame;

attaching a portion of the frame to the panel; and forming the panel into a tubular shape.

6. A method of constructing a knee support comprising the steps of:

providing a first elastically deformable material having a thickness;

forming a panel from said deformable material;

providing a second elastically deformable material having a thickness substantially the same as the thickness of the first elastically deformable material;

forming a frame of a said second elastically deformable material having an opening therein sized and shaped to receive an insert;

providing a third elastically deformable material having a thickness that is thinner than said second elastically deformable material;

forming said insert of said third elastically deformable material;

attaching said insert to said frame to cover the opening;

attaching said frame to the panel; and forming the panel into a tubular shape.

7. The method of claim 6, wherein the insert is attached to the frame so that the insert will be in tension in the frame.

8. The method of claim 7 comprising the further step of forming one or more darts in the panel such that the knee support will be bent at a preselected angle.

9. A support for use about a body joint from which a first body member extends and is movable in a preselected direction relative to a second body member extending from the body joint, the support comprising:

a sleeve having open opposite ends and sized and shaped to snugly fit about said body joint, said sleeve having a first opening formed therein for positioning proximate the body joint and said sleeve being formed of an elastically-deformable, closed-cell, neoprene-type material having a thickness;

a first insert sized and shaped to fit in and secured in said first opening in tension to urge relative movement of said first body member relative to said second body member in a preselected direction, said first insert being formed of an elastically-deformable material thinner in thickness than said sleeve material; and a second insert formed of an elastically-deformable material interpositioned between said first opening and said first insert and secured thereinbetween.

10. A knee support, comprising:

a sleeve having opposite ends and formed of an elastically-deformable material, said sleeve being sized and shaped for positioning about the knee and having a first opening formed therein at a position proximate the longitudinal center point between said opposite ends for positioning proximate the popliteal area of the knee;

an insert secured in said first opening of said sleeve, said insert being formed of a porous, elastically-deformable material that is thinner than the elastically-deformable material of said sleeve; and a second insert formed of elastically-deformable material of substantially the same thickness as said elastically-deformable material of said sleeve and sized and shaped to be received in said first opening, said second insert having a second opening formed therein that is sized and shaped to receive said first insert therein.

11. The support of claim 10, further including means for bending the support in a preformed shape to more precisely conform to the shape of the knee.

12. The support of claim 11, wherein said bending means comprises one or more darts formed in said sleeve.

13. A compliant support for a knee joint, the knee joint having a popliteal area at the back thereof that is compressed during flexion, the support comprising:

a first panel of stretchable material formed into a tubular shape that is sized to fit over and conform to the shape of the knee joint;

a second panel of dissimilar resilient material that is thinner than said stretchable material of said first panel, said second panel of dissimilar material being attachable within an opening formed in said first panel and positioned so that it will be placed over the popliteal area of the knee joint when said support is worn and stretches when the knee joint is not flexed and relaxes during flexion of the knee joint to conform to the shape of the popliteal area and thereby eliminate bunching of material in the popliteal area of the knee joint and increase user comfort; and a frame formed of stretchable material that is substantially the same thickness as said first panel, said frame having an inside edge that defines an opening and an outside edge sized and shaped to be received in said opening in said first panel, and further said second panel of dissimilar material being attached to said inside edge of said frame to cover said opening, said frame being attached to said first panel of stretchable material.

* * * * *